United States Patent [19]

Otte et al.

[11] Patent Number: 4,551,564

[45] Date of Patent: Nov. 5, 1985

[54] PROCESS FOR THE PRODUCTION OF 2- AND 4-TERT-BUTYLCYCLOHEXANOLS WITH HIGH PROPORTIONS OF CIS-ISOMERS BY CATALYTIC-HYDROGENATION OF THE CORRESPONDING TERT-BUTYLPHENOLS

[75] Inventors: Werner Otte, Dorsten; Rudolf Nehring; Manfred zür Haüsen, both of Marl, all of Fed. Rep. of Germany

[73] Assignee: Chemische Werke Huels, AG, Marl, Fed. Rep. of Germany

[21] Appl. No.: 663,734

[22] Filed: Oct. 22, 1984

[30] Foreign Application Priority Data

Oct. 22, 1983 [DE] Fed. Rep. of Germany ....... 3338437
Jan. 17, 1984 [DE] Fed. Rep. of Germany ....... 3401343

[51] Int. Cl.$^4$ ............................................. C07C 35/08
[52] U.S. Cl. ................................... 568/834; 568/830; 568/832
[58] Field of Search ............... 568/832, 833, 834, 835, 568/830

[56] References Cited

U.S. PATENT DOCUMENTS

| | | | |
|---|---|---|---|
| 2,927,127 | 3/1960 | Sommerville et al. | 568/834 |
| 3,124,614 | 3/1964 | Dankert et al. | 568/834 |
| 4,162,267 | 7/1979 | Fisher et al. | 568/835 |
| 4,212,990 | 7/1980 | Yasuhara et al. | 568/834 |
| 4,343,955 | 8/1982 | Oshima et al. | 568/834 |

FOREIGN PATENT DOCUMENTS

| | | | |
|---|---|---|---|
| 2132547 | 1/1973 | Fed. Rep. of Germany | 568/834 |
| 2016449 | 9/1979 | United Kingdom | 568/834 |

*Primary Examiner*—Werren B. Lone
*Attorney, Agent, or Firm*—Millen & White

[57] ABSTRACT

2- and 4-tert-butylcyclohexanols are produced having high proportions of cis-isomers, by hydrogenating the corresponding tert-butylphenols in the presence of Pd and Ru catalysts in two stages under hydrogen pressures of above 200 bar and at temperatures of 70°–280° C. In the first stage, a Pd catalyst is employed, and a Ru catalyst is used in the second stage.

18 Claims, No Drawings

PROCESS FOR THE PRODUCTION OF 2- AND 4-TERT-BUTYLCYCLOHEXANOLS WITH HIGH PROPORTIONS OF CIS-ISOMERS BY CATALYTIC-HYDROGENATION OF THE CORRESPONDING TERT-BUTYLPHENOLS

BACKGROUND OF THE INVENTION

The present invention relates to a process for the production of 2- and 4-tert-butylcyclohexanols by two-stage catalytic hydrogenation of the corresponding tertbutylphenols, which results in obtaining the cis-isomer in high proportions in the hydrogenation product.

Heretofore, it has been possible to obtain both 2- and 4-tert-butyl products with an increased proportion of cis-isomers only by a discontinuous process in solution. This, however, requires an additional purifying distillation stage (See British Patent No. 2,016,449=DOS No. 2,909,663, German Patent No. 2,132,547).

Since the 2- and 4-tert-butylcyclohexanols with high proportions of cis-isomers are of increasing economic interest, the problem resides in finding a process enabling the manufacture of both products with increased proportions of cis-isomers in a simple and economical fashion.

SUMMARY OF THE INVENTION

Therefore, it is an object of this invention to provide a process for economically preparing 2- and 4-tert-butylcyclohexanols having a high proportion of cis-isomers.

Upon further study of the specification and appended claims, further objects and advantages of this invention will become apparent to those skilled in the art.

These objects have been attained by this invention by providing a process for the production of 2- and 4-tert-butylcyclohexanols having high proportions of cis-isomers and of the formula

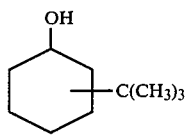

comprising hydrogenating the corresponding tert-butylphenols with hydrogen in the presence of Pd and Ru catalysts, wherein the hydrogenation is performed in two stages under hydrogen pressures of above 200 bar, and, in the first stage, on a Pd catalyst at temperatures of 120°-280° C. and, in the second stage, on a Ru catalyst at temperatures of 70°-200° C.

DETAILED DISCUSSION

Surprisingly, using the process of this invention, without need of solvents and without subsequent purification, the desired 2- and 4-tert-butylcyclohexanols with high cis proportions are obtained with a high yield and purity. Products having especially high cis proportions of up to 90% are achieved for 2-tert-butylcyclohexanol. For 2-tert-butylcyclohexanol, cis contents generally are about 75-90%, e.g., about 80-90%, preferably about 85-90%; for 4-tert-butylcyclohexanols, cis contents generally are 40-90%, e.g., 45-90%.

A particular advantage of the process of this invention is that the hydrogenation can be carried out continuously. The cis-rich tert-butylcyclohexanols prepared in accordance with this invention can be utilized directly for further processing, particularly for the manufacture of fragrances or fragrance products.

In a particularly advantageous process of this invention the 2- and 4-tert-butylphenols are first contacted, in a first stage, with hydrogen over a fixedly arranged Pd catalyst, for example, about 0.1-5% by weight, and preferably about 0.5-1% by weight Pd, on an inert support, e.g., $Al_2O_3$. The catalyst and support are preferably in the trickle phase. The catalyst is in a fixed bed. The feedstock is running from the top of the catalyst bed to the bottom together with the hydrogen. The process is carried out at a temperature of about 120°-280° C., preferably about 160°-220° C., and under a pressure of above 200 bar, preferably 250-350 bar. Preferably a portion of the hydrogenation product of the first stage is recycled to the feedstock upstream of the first stage reactor. The proportion of recycled hydrogenation product of the first stage is about one to 20 times, preferably about 5 to 10 times the quantity of the feed of raw material. The conversion of tert-butylphenols in this first stage is generally 65-98%, preferably about 80-90%.

The portion of the hydrogenation product that is not recycled, with the residual contents of tert-butylphenols, and tert-butylcyclohexanone as an intermediate product, is preferably hydrogenated in a second stage over a fixedly arranged Ru catalyst, for example, preferably 0.5-1% Ru on an inert support, e.g., $Al_2O_3$, preferably in the trickle phase, without recycling at a temperature of 70°-200° C., preferably 100°-150° C. and under a pressure of above 200 bar, preferably 250-350 bar, thereby rendering it essentially free of aromatics. The aromatic content ranges below 0.2%, preferably below 10 ppm.

In general, the process is conducted with feed quantities of 0.1-5 liters of feed/liter of catalyst . hour, preferably 0,2 to 2 liter of feed/liter of catalyst . hour.

In essence, any palladium or ruthenium metal catalyst can be utilized. Preferably, the catalyst will have a particle size in the range of 2-5 mm. Similarly, any reaction compatible inert material can be used as the catalyst carrier. Preferably, $Al_2O_3$ is used, most preferably having a particle size of 2-5 mm. Other contemplated equivalent carriers include silica, charcoal, etc.

A two-stage hydrogenation wherein a Pd catalyst is used in both stages does not make it possible to produce a tert-butylcyclohexanol with high proportions of cis-isomers, as demonstrated by Comparative Example A. Although this comparative process achieves a low content of aromatics, the hydrogenation product still contains considerable amounts of tert-butylcyclohexanone (e.g., 45-55%) which would have to be hydrogenated, in yet an additional hydrogenation process (e.g., a third stage), for example on CuCr catalysts to form the tert-butylcyclohexanols, whereby the final product becomes considerably more expensive than products produced in accordance with this invention.

A one-stage hydrogenation on Ru catalysts requires such strict hydrogenation conditions that the proportion of cis-isomers drops markedly as compared with the proportion of cis-isomers producible with the present process. With less strict conditions, rehydrogenation [i.e., post hydrogenation] is required (See Comparative Examples B and C). Furthermore, as demonstrated by Comparative Examples B and C, the throughput is substantially lower when using the Ru catalyst than in the case of the Pd catalyst.

The tert-butylcyclohexanols, having high proportions of cis-isomers, are obtained in high purity by this invention, so that they can be employed for the manufacture of fragrances without additional purification.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Per hour, 27 l of 2-tert-butylphenol (2-TBPHOL) is conducted with hydrogen at 200° C. and under a total pressure of 300 bar through a flow reactor (volume 20 l) filled with 20 l of a Pd catalyst (0.5% by weight Pd on $Al_2O_3$). A mixture is produced from 250 l/h of the hydrogenation product and the feed, and the mixture is passed through the reactor. The hydrogenation product, on the average, has the following composition:
0.3% tert-butylcyclohexane—(TBCAN)
60% 2-tert-butylcyclohexanone—(2-TBCON)
18% cis-2-tert-butylcyclohexanol—(cis-2-TBCOL)
5% trans-2-tert-butylcyclohexanol—(tr-2-TBCOL)
16.7% 2-tert-butylphenol—(2-TBPHOL)
400 ml of this hydrogenation product is conducted per hour with hydrogen through a second flow reactor (volume 400 ml) at 140° C. and under a total pressure of 300 bar; this reactor is filled with 400 ml of a Ru catalyst (0.5% by weight Ru on $Al_2O_3$).

The hydrogenation product has the following composition:
0.2% tert-butylcyclohexane—(TBCAN)
0.3% 2-tert-butylcyclohexanone—(2-TBCON)
85.1% cis-2-tert-butylcyclohexanol—(cis-2-TBCOL)
14.4% trans-2-tert-butylcyclohexanol—(tr-2-TBCOL)
<10 ppm 2-tert-butylphenol—(2-TBPHOL)

EXAMPLE 2

The process is conducted as described in Example 1, but passing through the first reactor 40 l/h, instead of ¢l/h, of 2-TBPHOL at 220° C. instead of 200° C.

The hydrogenation product has the following composition:
0.1% TBCAN
58.2% 2-TBCON
8.7% cis-2-TBCOL
2.7% tr-2-TBCOL
30.3% 2-TBPHOL Per hour, 400 ml of this hydrogenation product from the first stage is hydrogenated in the second stage according to the description of Example 1.

The hydrogenation product shows the following composition:
0.1% TBCAN
0.2% 2-TBCON
83.4% cis-2-TBCOL
16.3% tr-2-TBCOL
<10 ppm 2-TBPHOL

EXAMPLE 3

According to the description in Example 1, 2-TBPHOL is hydrogenated in the first stage, but 17 l/h of 2-TBPHOL with 200 l/h of product recycling at 160° C., with the following result:
76.8% 2-TBCON
9.3% cis-2-TBCOL
2.4% tr-2-TBCOL
11.5% 2-TBPHOL Hydrogenation in the second stage takes place as disclosed in Example 1, with a comparable result.

EXAMPLE 4

2-TBPHOL is hydrogenated as set forth in Example 3, but at 170° C. in the first stage, with the following result:
75.8% 2-TBCON
15.4% cis-2-TBCOL
4.0% tr-2-TBCOL
4.8% 2-TBPHOL Hydrogenation in the second stage is performed as set forth in Example 1, with a comparable result.

EXAMPLE 5

2-TBPHOL is hydrogenated according to the disclosure in Example 3, but at 180° C. in the first stage, with the result as follows:
67.1% 2-TBCON
24.9% cis-2-TBCOL
6.4% tr-2-TBCOL
1.6% 2-TBPHOL Hydrogenation in the second stage is conducted according to the description of Example 1, with comparable result.

Comparative Example A

In the first stage, 2-TBPHOL is hydrogenated as set forth in Example 1. In the second reactor, the hydrogenation product of the first stage is hydrogenated at 150° C. over 400 ml of the Pd catalyst (0.5% Pd on $Al_2O_3$). On the average, the hydrogenation product of the second stage has the following composition:
0.3% TBCAN
44.3% 2-TBCON
45.7% cis-2-TBCOL
9.7% tr-2-TBCOL
<10 ppm 2-TBPHOL If the temperature is raised in the second stage from 150° C. to 200° C. until no 2-TBCON can be detected any longer, then the hydrogenation product of the second stage has the following composition:
1.8% 2-TBCAN
<0.1% 2-TBCON
62.7% cis-2-TBCOL
33.9% tr-2-TBCOL
95 ppm 2-TBPHOL
1.6% unknown compounds

EXAMPLE 6

Hydrogenation of 2-TBPHOL is conducted in the first stage according to the statements in Example 1. In the second stage, a Ru catalyst is utilized containing 1% Ru on $Al_2O_3$. The hydrogenation product obtained according to Example 1, stage 1, is hydrogenated on this Ru catalyst at 120 ° C. in an amount of 160 ml/h. The hydrogenation product from the second stage has the following composition, on the average:
0.3% TBCAN
81.7% cis-2-TBCOL
18.0% tr-2-TBCOL
<0.1% 2-TBPHOL

EXAMPLE 7

Hydrogenation is effected according to the disclosure of Example 3, but at 160° C. with a feed of 21 l/h of 2-TBPHOL and a recycling of 275 l/h of hydrogenation product, with the following result:
0.4% TBCAN
78.1% 2-TBCON
6.7% cis-2-TBCOL
1.9% tr-2-TBCOL
12.9% 2-TBPHOL Hydrogenation in the second stage takes place according to the description of Example 1, with comparable result.

EXAMPLE 8

Hydrogenation is conducted according to the description in Example 7, but recycling 150 l/h of hydrogenation product. In the first stage, a hydrogenation product is obtained having the following composition:
0.2% TBCAN
76.1% 2-TBCON
6.3% cis-2-TBCOL
1.8% tr-2-TBCOL
15.6% 2-TBPHOL Hydrogenation in the second stage is performed as set forth in Example 1, with a comparable result.

EXAMPLE 9

Hydrogenation in the first stage takes place according to the description in Example 1. In the second stage, hydrogenation is conducted at 100° C. with 200 ml/h of the hydrogenation product obtained in the first stage on the Ru catalyst used in Example 6 (1% Ru on $Al_2O_3$), thus obtaining a hydrogenation product having the following composition:
0.3% 2-TBCON
80.8% cis-2-TBCOL
18.9% tr-2-TBCOL
<0.1% 2-TBPHOL Hydrogenation in the second stage is performed as set forth in Example 1, with comparable result.

Comparative Example B

Per hour, 400 ml of pure 2-TBPHOL (i.e. first stage) is conducted at 100° C. and at 300 bar through the flow reactor, capacity 400 ml, utilized in Example 1 in the second stage, this reactor being filled with 400 ml of the Ru catalyst (1% on $Al_2O_3$) used in Example 6. On the average, the hydrogenation product has the following composition:
14.2% 2-TBCON
74.4% cis-2-TBCOL
11.2% tr-2-TBCOL
0.2% 2-TBPHOL

Comparative Example C

By conducting the hydrogenation according to the description in Comparative Example B, but at 180° C., the following results are obtained:
0.6% TBCAN
75.1% cis-2-TBCOL
24.3% tr-2-TBCOL
<10 ppm 2-TBPHOL

EXAMPLE 10

Per hour, 80 ml of pure 2-TBPHOL (i.e. first stage, without remixing) is conducted with hydrogen at 120° C. and 300 bar through the 400 ml reactor described in Example 1 (second stage), filled with 400 ml of the Pd catalyst indicated in Example 1. On the average, the hydrogenation product has the following composition:
64.1% 2-TBCON
27.0% cis-2-TBCOL
6.0% tr-2-TBCOL
2.9% 2-TBPHOL Hydrogenation in the second stage takes place as set forth in Example 1, with comparable result.

EXAMPLE 11

The process was conducted as in Example 1, but using a catalyst with 0.1% Pd on $Al_2O_3$. The feed of o-TBPHOL is, at 200° C. and 300 bar total pressure, 20 l/h, which is combined with 200 l/h of hydrogenation product. This hydrogenation product has the following composition, on the average:
0.1% 2-TBCAN
72.3% 2-TBCON
16.8% cis-2-TBCOL
3.3% tr-2-TBCOL
7.5% 2-TBPHOL Hydrogenation in the second stage is performed as indicated in Example 1, with comparable result.

EXAMPLE 12

The hydrogenation product of the first stage according to Example 1 is hydrogenated, in the 400 ml apparatus mentioned in Example 1 (second stage), on a catalyst containing 0.1% Ru on $Al_2O_3$. At 120° C., 300 bar, and a feed of 80 ml/h the final product has the following composition:
0.1% TBCAN
80.4% cis-2-TBCOL
19.5% tr-2-TBCOL
<10 ppm 2-TBPHOL

Comparative Example D

By conducting the hydrogenation as set forth in Example 1, but with 4-tert-butylphenol (4-TBPHOL) instead of with 2-tert-butylphenol, at a temperature of 195° C. instead of 200° C., and with a feed of 10 l/h instead of 27 l/h, as well as a remixing of 150 l/h instead of 250 l/h, then a hydrogenation product of the following composition is obtained in the first stage:
0.2% 4-TBCAN
4.0% 4-TBCON
28.1% cis-4-TBCOL
65.4% trans-4-TBCOL
2.1% 4-TBPHOL
0.2% unknown compounds The second stage is performed as described in Example 1, but hydrogenating the hydrogenation product of the first stage (400 ml/h), instead of using the Ru catalyst set forth therein, on the same Pd catalyst employed in the first stage, at a temperature of 210° C. instead of 140° C.

The hydrogenation product of the second stage has the following composition:
0.2% 4-TBCAN
<0.1% 4-TBCON
29.3% cis-4-TBCOL
70.3% trans-4-TBCOL
<0.01% 4-TBPHOL
0.2% unknown compounds

EXAMPLE 13

The process of Example 1 is repeated, but using 4-tert-butylphenol (4-TBPHOL) in place of 2-tert-butylphenol, and hydrogenating in the first stage with a feed of 8 l/h instead of 27 l/h and at a temperature of 150° C. instead of 200° C. The hydrogenation product of the first stage has the following composition:
10.8% 4-TBCON
30.7% cis-4-TBCOL
27.4% trans-4-TBCOL
30.7% 4-TBPHOL
0.4% unknown compounds The second hydrogenation stage is conducted as set forth in Example 1, but with a feed of 120 ml/h of the hydrogenation product from the first stage, instead of with 400 ml, and at a temperature of 150° C. instead of 140° C.

The hydrogenation product of the second stage has, on the average, the following composition:
0.2% 4-TBCAN
— 4-TBCON
46.4% cis-4-TBCOL
53.1% trans-4-TBCOL
<0.01% 4-TBPHOL
0.3% unknown compounds The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of 2- or 4-tertbutylcyclohexanol having a high proportion of cis-isomers comprising hydrogenating the corresponding tert-butylphenol in two stages under hydrogen pressures of above 200 bar in each stage, and, in the first stage, on a Pd metal catalyst at a temperature of 120°-280° C. and, in the second stage, on a Ru metal catalyst at a temperature of 70°-200° C.

2. A process of claim 1, wherein the hydrogenation in the first stage is carried out at a temperature of 160°-220° C. and the hydrogenation in the second stage is carried out at a temperature of 100°-150° C.

3. A process of claim 2, wherein at least one hydrogenation stage is carried out under a pressure of 250-350 bar.

4. A process of claim 3, wherein in said first stage, the tert-butylphenol is introduced continuously and the first stage product is recycled to the first stage, in an amount which is 1 to 20 times the amount of feed tert-butylphenol.

5. A process of claim 4, wherein the amount of product returned to said first stage is 5-10 times the amount of tert-butylphenol introduced to said first stage.

6. A process of claim 2, wherein the catalysts are supported on an inert carrier.

7. A process of claim 3, wherein the catalysts are supported on an inert carrier.

8. A process of claim 4, wherein the catalysts are supported on an inert carrier.

9. A process of claim 6, wherein the support is aluminum oxide.

10. A process of claim 7, wherein the support is aluminum oxide.

11. A process of claim 8, wherein the support is aluminum oxide.

12. A process of claim 9, wherein the catalyst is affixed to the carrier in a concentration of 0.1% to 5% by weight.

13. A procsss of claim 10, wherein the catalyst is affixed to the carrier in a concentration of 0.1% to 5% by weight.

14. A process of claim 11, wherein the catalyst is affixed to the carrier in a concentration of 0.1% to 5% by weight.

15. A process of claim 9, wherein the catalyst is affixed to the carrier in a concentration of 0.5%-1% by weight.

16. A process of claim 10, wherein the catalyst is affixed to the carrier in a concentration of 0.5%-1% by weight.

17. A process of claim 11, wherein the catalyst is affixed to the carrier in a concentration of 0.5%-1% by weight.

18. A process of claim 1, wherein the throughput is 0.1-5 liters of feed/liter of catalyst hour.

* * * * *